(12) United States Patent
Sekiguchi

(10) Patent No.: US 11,969,153 B2
(45) Date of Patent: Apr. 30, 2024

(54) ENDOSCOPE

(71) Applicant: OLYMPUS MEDICAL SYSTEMS CORP., Tokyo (JP)

(72) Inventor: Yuta Sekiguchi, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 154 days.

(21) Appl. No.: 17/408,377

(22) Filed: Aug. 21, 2021

(65) Prior Publication Data

US 2023/0056718 A1    Feb. 23, 2023

(51) Int. Cl.
  *A61B 1/005*    (2006.01)
  *A61B 1/00*    (2006.01)

(52) U.S. Cl.
  CPC .......... *A61B 1/0052* (2013.01); *A61B 1/0057* (2013.01)

(58) Field of Classification Search
  CPC . A61B 1/0052; A61B 1/0057; A61B 1/00124; A61B 1/00126; A61B 1/00042
  See application file for complete search history.

(56) References Cited

U.S. PATENT DOCUMENTS

| | | | | | |
|---|---|---|---|---|---|
| 5,373,317 | A * | 12/1994 | Salvati | ............... | G02B 23/2476 348/66 |
| 6,830,545 | B2 * | 12/2004 | Bendall | ............... | A61B 1/00052 600/102 |
| 7,956,888 | B2 * | 6/2011 | Karpen | ............... | G02B 23/2484 348/85 |
| 8,177,710 | B1 * | 5/2012 | Hosaka | ............... | A61B 1/05 600/146 |
| 2007/0188604 | A1 * | 8/2007 | Miyamoto | ......... | A61B 1/00052 348/65 |
| 2012/0184814 | A1 * | 7/2012 | Ebata | ............... | A61B 1/00105 600/109 |
| 2013/0060088 | A1 * | 3/2013 | Okamoto | ............. | A61B 1/0052 600/146 |
| 2017/0086651 | A1 * | 3/2017 | Sato | ............... | G02B 23/2476 |
| 2017/0354319 | A1 * | 12/2017 | Sato | ............... | A61B 1/00121 |

FOREIGN PATENT DOCUMENTS

| | | |
|---|---|---|
| JP | 2001-161626 A | 6/2001 |
| WO | 2012/117835 A1 | 9/2012 |

* cited by examiner

*Primary Examiner* — Anh T Nguyen
*Assistant Examiner* — Rynae E Boler
(74) *Attorney, Agent, or Firm* — Scully, Scott, Murphy & Presser, P.C.

(57) ABSTRACT

An endoscope includes an insertion portion including a bending portion, an operation portion including an operation lever, a grasping portion including an actuator, and a tube body, in a continuous manner. When the operation lever is tilted, the actuator pulls a wire, whereby the bending portion is bent in a vertical direction and a lateral direction. The actuator is arranged such that a center of gravity of a portion including the insertion portion, the operation portion, the grasping portion, and the tube body is within a range in which at least one of the fourth finger or the fifth finger of the hand grasping the grasping portion is positioned, in a longitudinal direction of the grasping portion.

7 Claims, 5 Drawing Sheets

ENDOSCOPE

BACKGROUND OF THE INVENTION

1. Field of the Invention

The present invention relates to an endoscope provided with an operation lever configured to be tilted.

2. Description of the Related Art

Conventionally, endoscopes have been widely used in the medical field and the industrial field.

An endoscope is provided with an elongated insertion portion to be inserted into a subject, and an operation portion provided continuously on a proximal end side of the insertion portion. In an endoscope including a bendable bending portion provided in the insertion portion, the operation portion is provided with an operation member for carrying out a bending operation, other various operation switches, and the like.

An endoscope provided with an operation lever configured to be tilted as the operation member has been proposed. A specific example of the operation lever configured to be tilted is a joystick which is used for, for example, controlling a bend of a vertically and laterally bendable endoscope.

International Publication WO 2012/117835 discloses an electrical bending endoscope including an operator configured to be tilted for a bending operation, and a motor configured to pull a wire according to the bending operation of the operator. The electrical bending endoscope eliminates the need for manually pulling the wire, and therefore a force required for operation can be reduced. In addition, owing to employing the joystick-type operator, a finely-tuned bending operation is enabled. However, the electrical bending endoscope increases slightly in size and weight due to the operator and the motor being provided.

SUMMARY OF THE INVENTION

An endoscope according to one aspect of the present invention includes an insertion portion having an elongated shape, the insertion portion being provided with a bending portion and including a wire installed inside the insertion portion, an operation portion provided continuously on a proximal end side of the insertion portion and including an operation lever, a grasping portion configured to be grasped by a hand, the grasping portion being provided continuously on a proximal end side of the operation portion and including an actuator provided inside the grasping portion, and a tube body connected to the grasping portion and including a signal cable installed inside the tube body, wherein, when the operation lever is tilted, the actuator pulls the wire, whereby the bending portion is bent in a vertical direction and a lateral direction, and the actuator is arranged such that a center of gravity of a portion including the insertion portion, the operation portion, the grasping portion, and the tube body is within a range in which at least one of a fourth finger or a fifth finger of the hand grasping the grasping portion is arranged, in a longitudinal direction of the grasping portion.

DETAILED DESCRIPTION OF THE PREFERRED EMBODIMENTS

Figure 1:
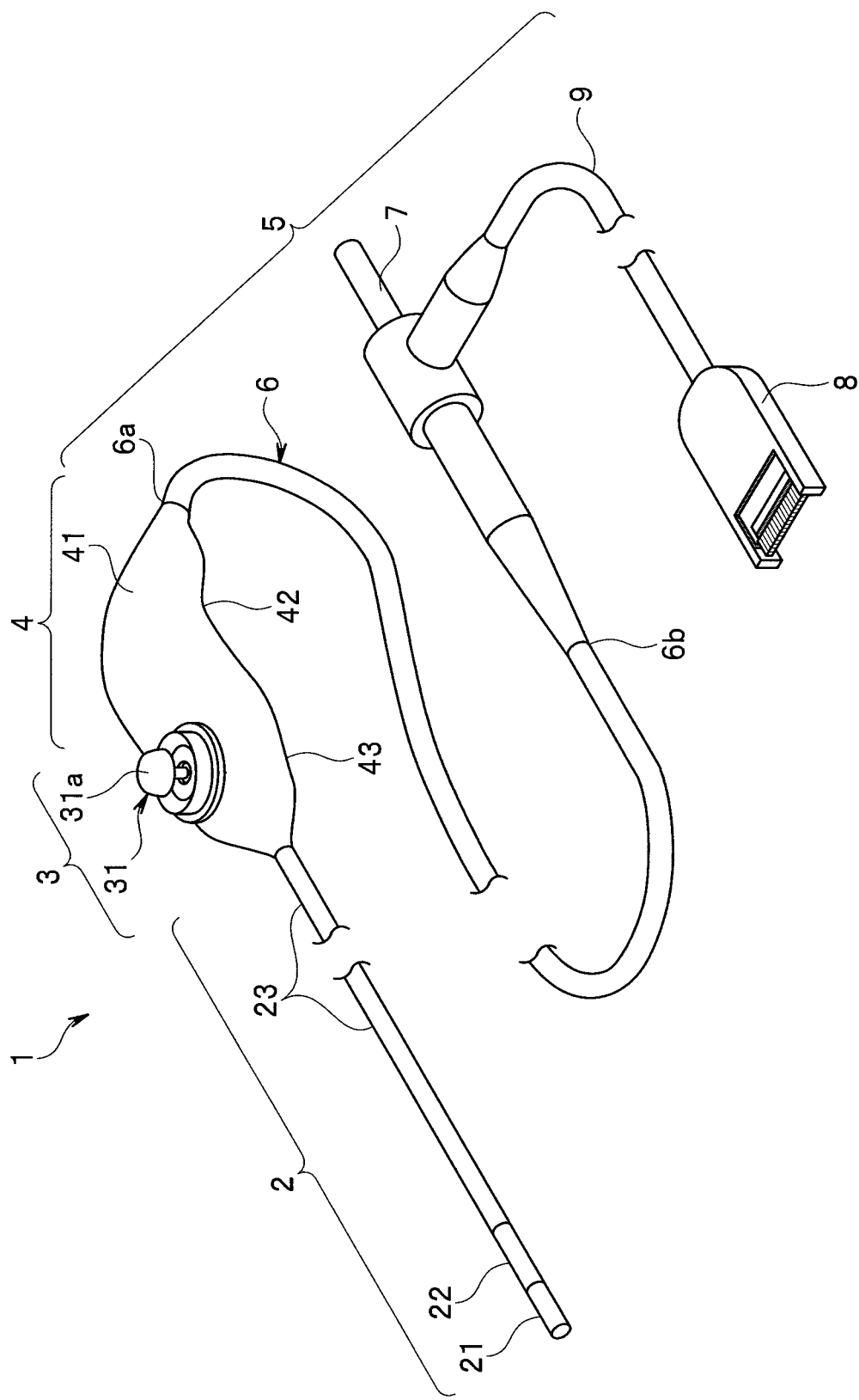
FIG. 1 is a perspective view of an example of a configuration of an endoscope according to a first embodiment of the present invention.

Hereinafter, embodiments of the present invention are described with reference to the drawings. However, the present invention is not limited to the embodiments described below.

Note that, in the drawings, identical or corresponding elements are referred to by the same reference symbol as appropriate. In each of the figures used for the following description, constitutive elements may have different scales in order that each of the constitutive elements have a recognizable size on the figures. The present invention is not limited to the number, shapes, ratios of size, and relative positional relationships of the constitutive elements featured in these figures.

First Embodiment

Figure 2:
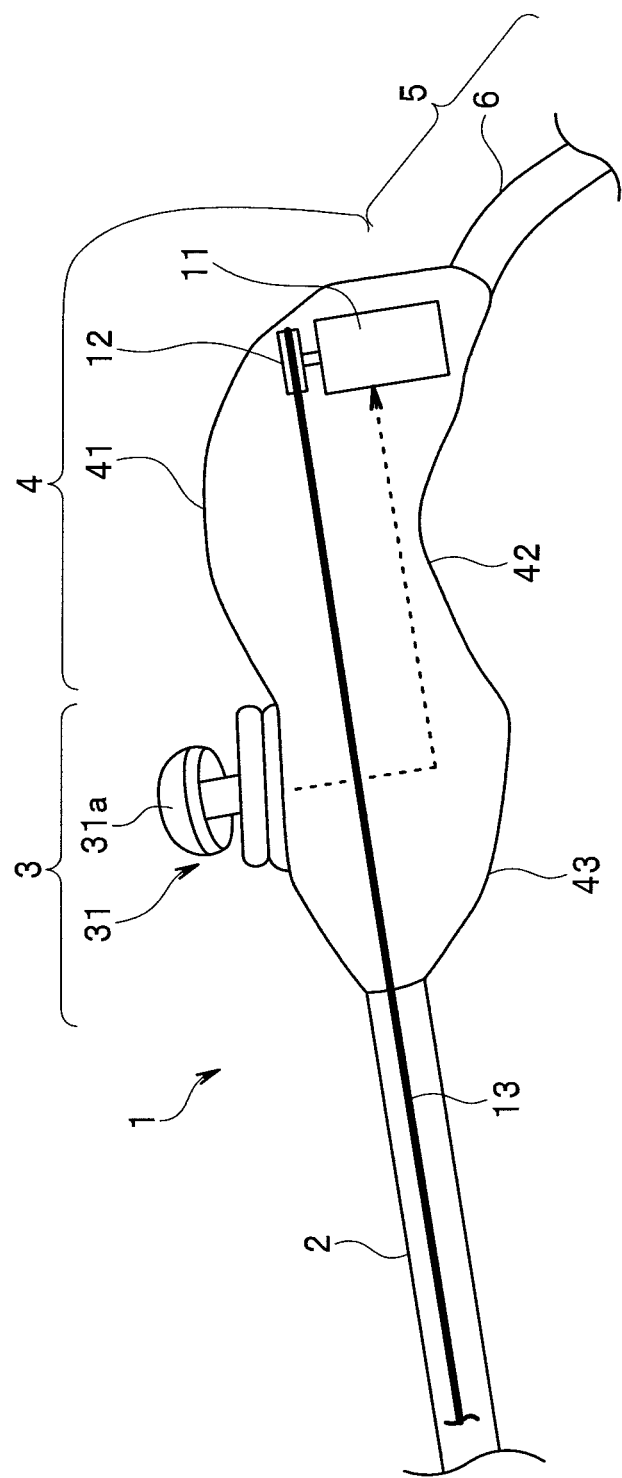
FIG. 2 is a diagram showing an example of arrangement of an actuator provided inside a grasping portion in the first embodiment.
Figure 3:
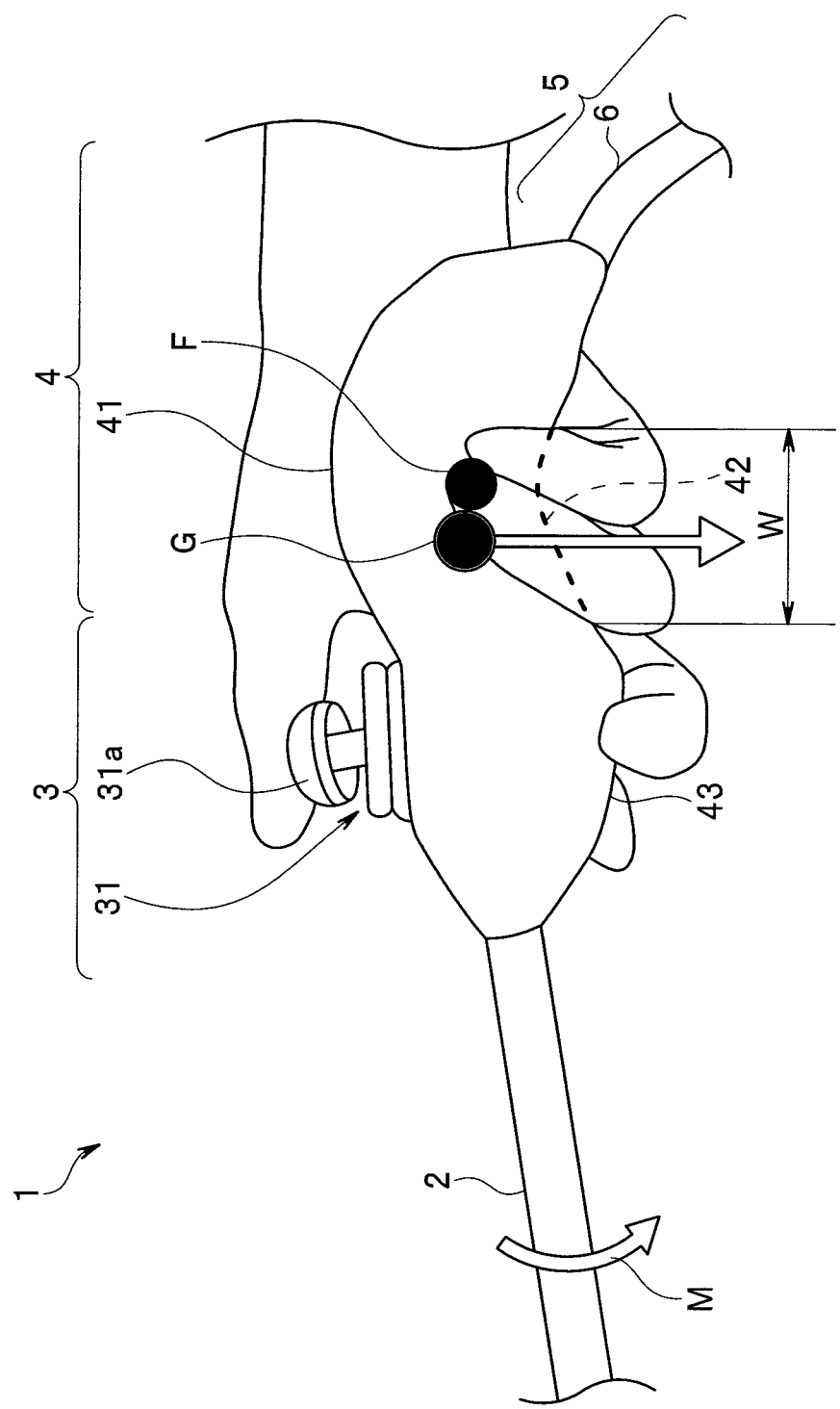
FIG. 3 is a diagram showing a manner of grasping the grasping portion of the endoscope of the first embodiment with the right hand.

FIG. 1 to FIG. 3 show the first embodiment of the present invention, and FIG. 1 is a perspective view of an example of a configuration of an endoscope 1 according to the present embodiment.

The endoscope 1 includes an elongated insertion portion 2 to be inserted into a subject, an operation portion 3 provided continuously on a proximal end side of the insertion portion 2, a grasping portion 4 provided continuously on a proximal end side of the operation portion 3, and a universal cable 5 extending from the grasping portion 4. Note that the subject into which the insertion portion 2 is inserted may be either a living being such as a human and an animal, or a non-living material such as a machine and a construction.

A distal end portion 21, a bending portion 22, and a tubular portion 23 are continuously provided in order from a distal end to a proximal end in the insertion portion 2.

The endoscope 1 is configured as, for example, an electronic endoscope in which an image pickup apparatus configured to pick up an image of the subject is arranged inside the distal end portion 21. The image pickup apparatus has a general well-known structure and therefore illustration of the structure is omitted. The image pickup apparatus includes an image pickup optical system configured to form an optical image of the subject, and an image sensor configured to carry out photoelectric conversion of the optical image thus formed and to output an image pickup signal. As the image sensor, for example, a solid-state image pickup device such as a CCD image sensor and a CMOS image sensor is suitably used. The image pickup signal is processed by an endoscope processor, which is an external device, via a signal cable connected to the image sensor.

An illumination window, which is not illustrated, configured to emit illumination light to the subject is provided in the distal end portion 21. The illumination light is emitted by a light source device, which is an external device of the endoscope 1, and transmitted through an optical fiber cable, which is provided inside the insertion portion 2 and not illustrated, to reach the illumination window.

The signal cable and the optical fiber cable are provided inside the insertion portion 2, the operation portion 3, the grasping portion 4, and the universal cable 5, and connected to the external device.

The bending portion 22 is configured to be bendable in the vertical direction and the lateral direction. A distal end portion of a wire 13 (see FIG. 2) provided inside the insertion portion 2 is fixed to the bending portion 22. A proximal end portion of the wire 13 is connected to a driving mechanism including an actuator 11 (see FIG. 2) provided inside the operation portion 3 or the grasping portion 4. The driving mechanism is configured to be driven according to a tilt operation of the operation lever 31, described later, provided in the operation portion 3 to pull the wire 13. Pulling the wire 13 bends the bending portion 22. Therefore, the endoscope 1 is an electrical bending endoscope.

The tubular portion 23 is a tubular section joining a proximal end of the bending portion 22 with a distal end of the operation portion 3. The tubular portion 23 may have either a rigid configuration in which the insertion portion 2 does not bend, or a flexible configuration in which the insertion portion 2 bends according to a shape of the subject into which the insertion portion 2 is inserted. An endoscope with an insertion portion having the rigid configuration is generally referred to as a rigid endoscope, while an endoscope with an insertion portion having the flexible configuration is generally referred to as a flexible endoscope. For example, the rigid endoscope and the flexible endoscope in the medical field are defined by ISO 8600-1:2015.

The operation portion 3 is provided continuously on the proximal end side of the insertion portion 2 and includes an operation lever 31. The operation lever 31 protrudes operably from an outer surface of the operation portion 3. The operation lever 31 is configured as, for example, a joystick, and includes, at a head section of a rod-shaped stick, a finger rest-shaped portion 31a on which the first finger of the hand grasping the grasping portion 4 is placed. The operation lever 31 is in a neutral position when the tilt operation is not being made. When a pressing force is applied on the finger rest-shaped portion 31a to carry out the tilt operation on the operation lever 31 from the neutral position, the operation lever 31 outputs an operation signal corresponding to a tilt direction and a tilt angle. When the driving mechanism receives the operation signal, the driving mechanism pulls the wire 13 according to the tilt direction and the tilt angle of the operation lever 31, such that the bending portion 22 is bent in the vertical direction and the lateral direction.

Note that, as used hereinafter, a face of the operation portion 3 (and the grasping portion 4) on which the operation lever 31 is provided is referred to as an upper face, a face on the opposite side of the upper face is referred to as a lower face, and, of two faces between the upper face and the lower face, a face on the right side when facing the distal end side is referred to as a right lateral face, and a face on the left side when facing the distal end side is referred to as a left lateral face, respectively.

In FIG. 1, the operation lever 31 is shown as the operation member provided in the operation portion 3, and other operation members are omitted. However, in addition to the operation lever 31, a bent holding lever configured to maintain an operated state of the operation lever 31, and operation buttons configured to control the operation of the image pickup apparatus may also be provided in the operation portion 3. The bent holding lever is an operation member configured to, in a free position, enable free operation of the operation lever 31, and, in a holding position, retain the position of the operation lever 31 and in turn fix the shape of the bending portion 22.

The grasping portion 4 is a section provided continuously on the proximal end side of the operation portion 3 and configured to be grasped by a hand. Inside the grasping portion 4, the actuator 11 is provided as shown in FIG. 2. FIG. 2 is a diagram showing an example of arrangement of the actuator 11 provided inside the grasping portion 4, and FIG. 3 is a diagram showing a manner of grasping the grasping portion 4 of the endoscope 1 with the right hand. Hereinafter, an example of grasping the grasping portion 4 with the right hand is explained. However, the grasping portion 4 may also be grasped by the left hand.

Note that, although FIG. 1 to FIG. 3 schematically show an example in which the grasping portion 4 is configured with a smoothly curved face, the present invention is not limited to such a configuration. For example, a cross-sectional shape of the grasping portion 4 perpendicular to the longitudinal direction may be a rectangular shape (rectangular shape of which shorter sides are cross sections of the upper face and the lower face, and of which longer sides are cross sections of the right lateral face and the left lateral face), may be a shape in which cross sections of the right lateral face and the left lateral face are straight lines and cross sections of the upper face and the lower face are arc-like, or may be an oval shape.

Supposing that the right lateral face of a surface 41 of the grasping portion 4 is grasped in such a way that the right lateral face is wrapped by the palm of the right hand, such that the operation lever 31 can be operated with the first finger, a first step 42 (first shaped portion) on which at least one (preferably both) of the fourth finger or the fifth finger of the hand grasping the grasping portion 4 is placed is provided on the lower face of the grasping portion 4. The first step 42 is positioned on the proximal end side with respect to the operation lever 31.

At least one of the second finger or the third finger of the hand grasping the grasping portion 4 can be placed on a lower face 43 on the distal end side with respect to the first step 42. Therefore, the grasping portion 4 extends to a portion facing the operation lever 31, on the lower face side.

FIG. 2 shows the driving mechanism in a simplified manner. In the example shown in FIG. 2, the actuator 11 constituting the driving mechanism is provided on the proximal end side, that is a side closer to the universal cable 5, of the grasping portion 4. The driving mechanism further includes a gear mechanism, which is not illustrated, configured to slow down the driving force of the actuator 11, and a pulley 12 configured to be rotated by the driving force transmitted from the gear mechanism to pull the wire 13. The gear mechanism and the pulley 12 are also provided on the proximal end side of the grasping portion 4, for example.

Among members arranged inside the operation portion 3 and the grasping portion 4, the driving mechanism is relatively heavy in weight. Given this, by providing the driving mechanism on, for example, the proximal end side of the grasping portion 4, the position of a center of gravity G of the portion including the insertion portion 2, the operation portion 3, the grasping portion 4, and a tube body 6 is adjusted in the longitudinal direction of the operation portion 3 and the grasping portion 4.

In other words, as shown in FIG. 3, the driving mechanism including the actuator 11 is arranged such that the center of gravity G of the portion including the insertion portion 2, the operation portion 3, the grasping portion 4, and the tube body 6 is within a range W in which at least one of the fourth finger or the fifth finger of the hand grasping the grasping portion 4 is positioned, in the longitudinal direction of the grasping portion 4. The center of gravity G is positioned, for example, in the first step 42 or on the inner side of the grasping portion 4 in the first step 42.

The distal end side of the wire 13 hung on the pulley 12 is connected to, for example, a bending piece at the distal end among a plurality of bending pieces provided in the bending portion 22. When the wire 13 is pulled, the bending piece at the distal end is pulled, whereby the bending portion 22 is bent. Note that, although the wire 13 is shown in a simplified manner in FIG. 2, the wire 13 is provided in a plurality of number (for example, four to correspond to the vertical and lateral bending directions of the bending portion 22.

The universal cable 5 extends from the proximal end of the grasping portion 4. The universal cable 5 includes the tube body 6, a light source connection portion 7, an electric connection portion 8, and a connection cable 9.

The tube body 6 is, for example, a flexible elongated tube. The signal cable and an optical fiber cable or the like are provided inside the tube. A distal end 6a of the tube body 6 is connected to the proximal end of the grasping portion 4, while a proximal end 6b of the tube body 6 is connected to the light source connection portion 7.

The light source connection portion 7 is a section connected to a light source device. In the light source connection portion 7, a proximal end of the optical fiber cable is exposed. By attaching the light source connection portion 7 to the light source device, the illumination light emitted from the light source device is incident to the proximal end of the optical fiber cable. The optical fiber cable transmits the incident illumination light to the distal end portion 21 via the universal cable 5, the grasping portion 4, the operation portion 3, and the insertion portion 2. The illumination light emitted from the distal end of the optical fiber cable is emitted to the subject from the illumination window provided in the distal end portion 21.

The connection cable 9 is, for example, a flexible elongated tube. The signal cable is provided inside the tube. The connection cable 9 extends from the light source connection portion 7. The electric connection portion 8 is provided at an extension end of the connection cable 9. Note that, although FIG. 1 shows an example in which the light source connection portion 7 and the electric connection portion 8 are separated, the light source connection portion 7 and the electric connection portion 8 may be integrally configured in the case in which, for example, the light source device and the endoscope processor are configured as an integral instrument.

The electric connection portion 8 is a plug-like section provided with a plurality of electric contacts, and is connected to a receptacle portion provided in the endoscope processor. Attaching the electric connection portion 8 to the endoscope processor electrically connects the image pickup apparatus with the endoscope processor via the signal cable. The endoscope processor carries out various processes such as demosaicking, noise correction, color correction, contrast correction, and gamma correction to the image pickup signal outputted from the image pickup apparatus, for conversion to a displayable video signal. The video signal thus converted is outputted from the endoscope processor to a monitor, whereby an endoscopic image is displayed on the monitor.

As described above, when the endoscope 1 is in use, the light source connection portion 7, the electric connection portion 8, and the connection cable 9 that connects the light source connection portion 7 with the electric connection portion 8 in the universal cable 5 are in a state of being connected to an external device. In other words, loads of the light source connection portion 7, the electric connection portion 8, and the connection cable 9 are applied to the light source device and the endoscope processor, not to the hand grasping the endoscope 1. Therefore, the load applied to the hand grasping the endoscope 1 is due to the insertion portion 2, the operation portion 3, the grasping portion 4, and the tube body 6.

Next, a moment M of force in the case of grasping and operating the endoscope 1 is described.

In the state shown in FIG. 3, the grasping portion 4 is firmly held with the palm placed on the lateral face of the surface 41 of the grasping portion 4, and at least one of the fourth finger or the fifth finger (in the example shown in FIG. 3, both of the fourth finger and the fifth finger) placed on the first step 42. The load of the endoscope 1 in the gravity direction is applied to the fourth finger and the fifth finger supporting on the lower face side. Therefore, a fulcrum F in the case of grasping the endoscope 1 is positioned in the first step 42 with which at least one of the fourth finger or the fifth finger is in contact.

The operation lever 31 is arranged in such a position that the first finger of the hand grasping the grasping portion 4 operates the operation lever 31. The operation lever 31 is operated in a state in which the first finger presses the finger rest-shaped portion 31a, whereby a pressing force is applied from the first finger to the operation lever 31 during operation.

Supposing that the center of gravity G of the portion including the insertion portion 2, the operation portion 3, the grasping portion 4, and the tube body 6, i.e., the source of the load applied to the hand grasping the endoscope 1, was in a position on the distal end side with respect to the fulcrum F, away from the fulcrum F, the moment M (shown by an arc-shaped arrow in FIG. 3) of the force generated around the fulcrum F would be a synthesis of a first moment component due to the pressing force applied to the operation lever 31 from the first finger, and a second moment component due to the gravity applied to the center of gravity G (shown by a downward open arrow in FIG. 3). As the center of gravity G gets away from the fulcrum F toward the distal end side, the second moment component, and in turn the moment M of the synthesized force, increase. As a result, the operator who operates the endoscope 1 needs to restrain the distal end side of the endoscope 1 from rotating downward around the fulcrum F. This makes the operation of the endoscope 1 difficult. This also places a burden on the wrist and the like of the hand grasping the endoscope 1, making the operator more likely to be tired from a prolonged operation.

To the contrary, in the present embodiment, arrangement of the driving mechanism including the actuator 11 is adjusted in such a way that the position of the center of gravity G in the longitudinal direction of the grasping portion 4 is within a range W in which at least one of the fourth finger or the fifth finger of the hand grasping the grasping portion 4 is positioned. As a result, the center of gravity G is positioned in the first step 42 or on the inner side of the grasping portion 4 in the first step 42, whereby the position of the grasping portion 4 in the longitudinal direction corresponds to, or approximates to, the fulcrum F.

This enables suppression of the second moment component to 0 or a value close to 0, whereby the moment M of force can be reduced. In this case, it is more preferable that the position of the center of gravity G should correspond to the position of the fulcrum F in the longitudinal direction of the grasping portion 4, resulting in the second moment component being 0. By placing at least one of the second finger or the third finger of the hand grasping the grasping portion 4 on the lower face 43 on the distal end side with respect to the first step 42, the first moment component generated by the first finger pressing the finger rest-shaped portion 31a can be borne.

According to the first embodiment described above, positioning the center of gravity G in the vicinity of the fulcrum F reduces the moment M of force and in turn alleviates the burden on the wrist. By matching the positions of the center of gravity G and the fulcrum F in the longitudinal direction, the second moment component becomes 0 and the moment M of force is minimized, whereby the burden on the grasping hand is further alleviated. The endoscope 1 is thus achieved that is easy for an operator to operate and makes prolonged use less tiring.

Second Embodiment

Figure 4:
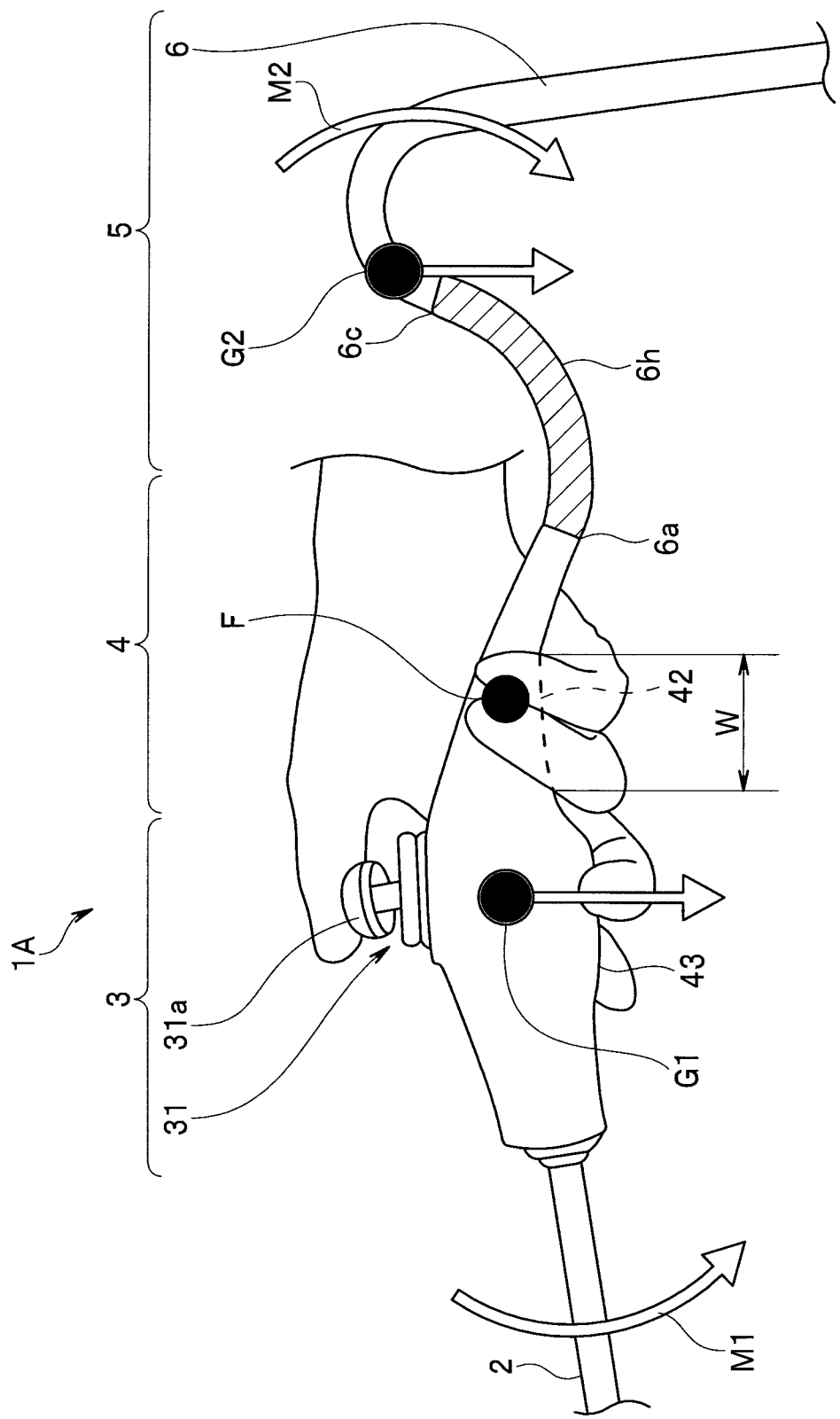
FIG. 4 is a diagram showing an example of a configuration of an endoscope according to a second embodiment of the present invention.

FIG. 4 is a diagram of the second embodiment of the present invention, showing an example of a configuration of an endoscope 1A. With regard to the second embodiment, elements similar to the elements of the first embodiment are denoted by the same reference symbols or the like and description of these elements is omitted as appropriate, and differences from the first embodiment are principally explained.

In the first embodiment described above, the driving mechanism including the actuator 11 is arranged inside the grasping portion 4, to position the center of gravity G in the vicinity of the fulcrum F. To the contrary, in the present embodiment, a rigid tube body 6h is provided in a portion of the tube body 6 adjacent to the grasping portion 4 in order to adjust a center of gravity G2 on the proximal end side with respect to the fulcrum F including the tube body 6, to position the center of gravity G in the vicinity of the fulcrum F.

As shown in FIG. 4, the present embodiment eliminates the need for employing a layout for arranging the actuator 11 inside the grasping portion 4, and therefore the grasping portion 4 is formed smaller than in the first embodiment. Therefore, the actuator 11 may be arranged inside the operation portion 3.

In such a configuration, the center of gravity G1 of a portion including the insertion portion 2 and the operation portion 3, on the distal end side with respect to the fulcrum F, is in a position similar to the position of the operation lever 31 in the longitudinal direction of the operation portion 3 and the grasping portion 4, for example (position on the distal end side with respect to the fulcrum F).

In addition, the rigid tube body 6h, of which shape is retained during grasping and operating the endoscope 1, is provided between the distal end 6a of the tube body 6 and a position 6c at a predetermined length from the distal end 6a toward the proximal end side along the tube body 6. Portions of the tube body 6 other than the rigid tube body 6h flexibly change in shape as described above. Therefore, a portion of the tube body 6 on the proximal end side with respect to the rigid tube body 6h is in a state of sagging under gravity.

Note that the rigid tube body 6h is not limited to the type with a fixed shape, and may be of the type with a deformable shape such as a standing tube. The standing tube can maintain a fixed bent state and is resistant to repeated bending. Given this, using the standing tube as the rigid tube body 6h enables a desirably deformed shape to be maintained during grasping and operating the endoscope 1. Therefore, the operator can deform the rigid tube body 6h to a shape facilitating operation of the endoscope 1.

The center of gravity G2 on the proximal end side with respect to the fulcrum F including the tube body 6 is in a position on the proximal end side with respect to the fulcrum F in the longitudinal direction of the tube body 6, as shown in FIG. 4. The center of gravity G2 is set as follows.

When a moment of force generated by the center of gravity G1 around the fulcrum F is referred to as M1, and a moment of force generated by the center of gravity G2 around the fulcrum F is referred to as M2, the position of the center of gravity G2 is set such that the moment M1 of force and the moment M2 of force have substantially the same magnitude and opposite orientation around the fulcrum F. As a result, the moments compensate each other and a sum of the moment M1 of force and the moment M2 of force can thus be suppressed to 0 or a value close to 0, whereby the burden on the grasping hand can be alleviated. In this case, the position of the center of gravity G in the vicinity of the fulcrum F is within the range W in which at least one of the fourth finger or the fifth finger of the hand grasping the grasping portion 4 is positioned.

Note that the position of the center of gravity G2 can be desirably set through adjusting the length and the shape of the rigid tube body 6h. For example, when the rigid tube body 6h is longer, the position where the flexible portion of the tube body 6 sags is positioned closer to the proximal end side, whereby the position of the center of gravity G2 can be positioned away from the fulcrum F to the proximal end side. To the contrary, when the rigid tube body 6h is shorter, the position where the flexible portion of the tube body 6 sags is positioned closer to the distal end side, whereby the position of the center of gravity G2 can be positioned close to the fulcrum F.

According to the second embodiment, substantially the same effect as the first embodiment described above is produced, and in addition, the burden on the hand grasping the grasping portion 4 can be alleviated even in the case in which it is difficult, from the viewpoint of design, to arrange the driving mechanism including the actuator 11 inside the grasping portion 4. Furthermore, the position of the center of gravity G2 can be desirably set through adjusting the length and the shape of the rigid tube body 6h, whereby an acceptable range for the position of the center of gravity G1 is broadened, and in turn the degree of freedom of design is increased for the operation portion 3, the grasping portion 4, and the like.

Third Embodiment

Figure 5:
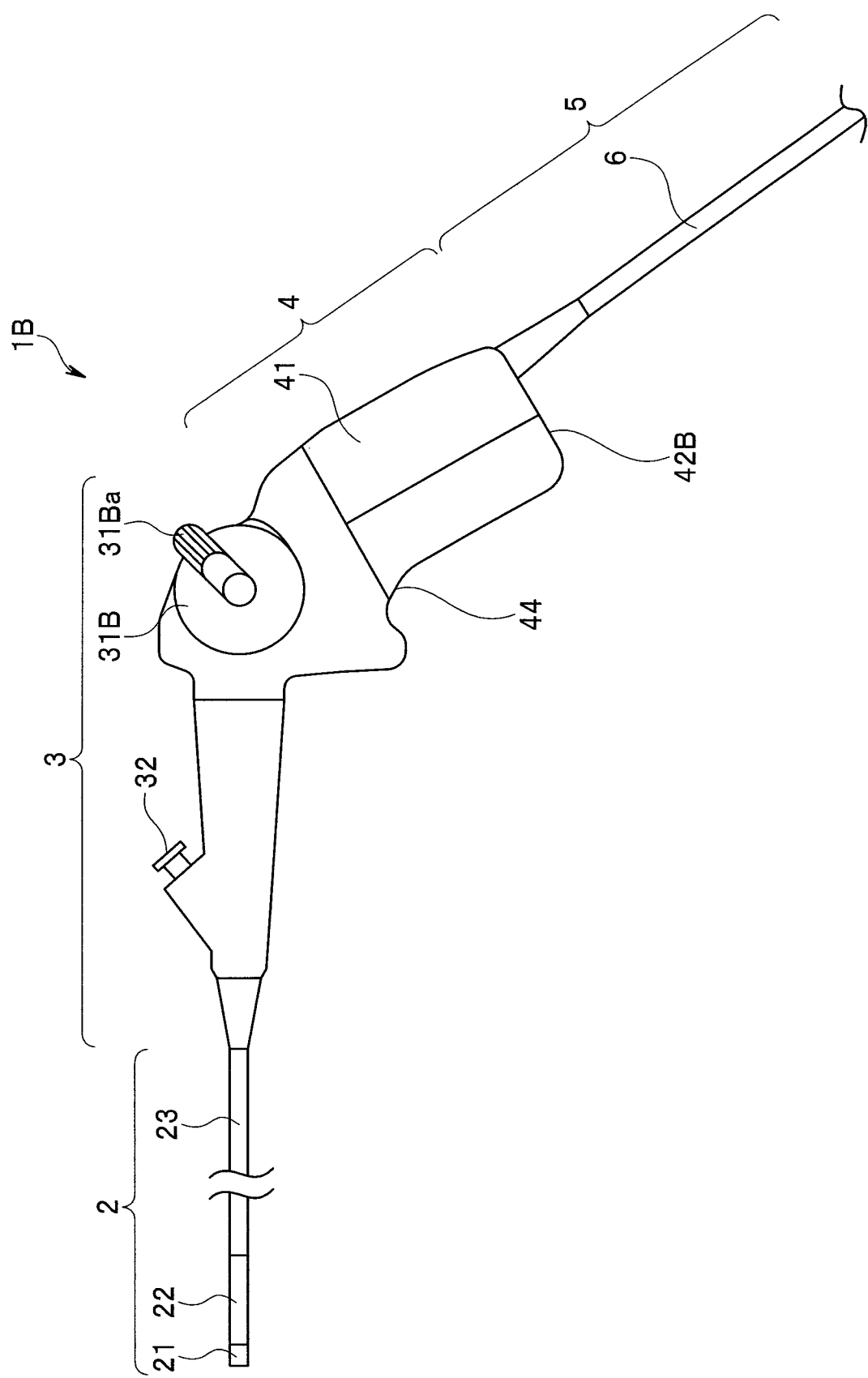
FIG. 5 is a diagram showing an example of a configuration of an endoscope according to a third embodiment of the present invention.

FIG. 5 is a diagram of the third embodiment of the present invention, showing an example of a configuration of an endoscope 1B. With regard to the third embodiment, elements similar to the elements of the first and second embodiments are denoted by the same reference symbols or the like and description of these elements is omitted as appropriate, and differences from the first and second embodiments are principally explained.

The endoscope 1B of the present embodiment is provided with a gun-grip type grasping portion 4.

The operation portion 3 of the endoscope 1B is provided with an operation lever 31B having a shape different from the shapes in the first and second embodiments. The operation lever 31B is an operation member configured to bend the bending portion 22 in response to a tilt operation, provided with a finger rest-shaped portion 31Ba on which the first finger of the hand grasping the grasping portion 4 is placed.

A treatment instrument insertion opening 32, through which a treatment instrument is to be inserted, is provided on the distal end side with respect to the operation lever 31B in the operation portion 3.

Supposing that the surface 41 of the grasping portion 4 is grasped in such a way that the surface 41 is wrapped by, for example, the palm of the right hand, such that the operation lever 31 can be operated with the first finger, a first step 42B (first shaped portion) on which at least one of the fourth finger or the fifth finger of the hand grasping the grasping portion 4 is placed is provided on the lower face of the grasping portion 4. The first step 42B is positioned on the proximal end side with respect to the operation lever 31B.

In a position adjacent to the operation portion 3 in the grasping portion 4, a second step 44 (second shaped portion) is further provided, on which at least one of the second finger or the third finger of the hand grasping the grasping portion 4 is placed.

The grasping portion 4 of the present embodiment has a relatively spacious inner space, and the actuator 11 can be arranged inside the grasping portion 4 as in the first embodiment. The center of gravity G of the portion including the insertion portion 2, the operation portion 3, the grasping portion 4, and the tube body 6 is thus positioned in the vicinity of the first step 42B, which functions as the fulcrum F. However, in the present embodiment as well, the rigid tube body 6h may be provided to increase the degree of freedom of layout of the operation portion 3 and the grasping portion 4 as in the second embodiment.

According to the third embodiment, substantially the same effect as the first and second embodiments described above can be produced, also in the endoscope 1B provided with the gun-grip type grasping portion 4.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
an insertion portion having an elongated shape, the insertion portion comprising a bending portion and a bending wire provided inside the insertion portion;
an operation portion provided proximally relative to the insertion portion and including an operation lever operatively connected to the bending wire;
a grasping portion provided proximally relative to the operation portion and including an actuator provided inside the grasping portion; and
a tube body connected to the grasping portion and including a signal cable provided inside the tube body, wherein
the actuator is positioned within the grasping portion such that a center of gravity of the insertion portion, the operation portion, the grasping portion, and the tube body is proximal to the operation lever, in a longitudinal direction of the grasping portion;
the operation lever being disposed on a first outer surface of the operation portion;
the grasping portion having a second outer surface opposing the first outer surface relative to a longitudinal axis of the grasping portion, the second outer surface having a concavity provided proximally relative to the operation lever and being concave relative to the longitudinal axis of the grasping portion;
the longitudinal axis of the grasping portion is a first longitudinal axis, the operation portion having a second longitudinal axis intersecting with the first longitudinal axis; and
the center of gravity is positioned at a proximal-most end of the grasping portion.

2. The endoscope according to claim 1, wherein the tube body comprises a rigid tube body portion, the rigid tube body portion is provided in a position adjacent to the grasping portion, the rigid tube body portion having a greater rigidity than other portions of the tube body.

3. The endoscope according to claim 1, wherein the actuator is configured to pull the bending wire when the operation lever is tilted to bend the bending portion in a vertical direction and in a lateral direction.

4. The endoscope according to claim 1, wherein the actuator comprises a driving mechanism provided on a proximal side of the grasping portion.

5. The endoscope according to claim 4, wherein the driving mechanism comprises a pulley.

6. The endoscope according to claim 1, wherein the actuator is provided proximally relative to a center of the concavity.

7. The endoscope according to claim 1, wherein the actuator is positioned such that a total moment acting to rotate the insertion portion is substantially zero, the total moment being a combination of a first moment component due to a pressing force applied to the operation lever, and a second moment component due to gravity acting at the center of gravity.

* * * * *